United States Patent
Lee

(10) Patent No.: US 10,123,779 B2
(45) Date of Patent: Nov. 13, 2018

(54) METHOD AND APPARATUS FOR GENERATING ULTRASOUND IMAGE HAVING ENHANCED QUALITY

(71) Applicant: SAMSUNG MEDISON CO., LTD., Gangwon-do (KR)

(72) Inventor: Jae-Sung Lee, Gangwon-do (KR)

(73) Assignee: SAMSUNG MEDISON CO., LTD., Hongcheon-gun, Gangwon-do (KR)

( * ) Notice: Subject to any disclaimer, the term of this patent is extended or adjusted under 35 U.S.C. 154(b) by 907 days.

(21) Appl. No.: 14/591,815

(22) Filed: Jan. 7, 2015

(65) Prior Publication Data

US 2015/0250454 A1 Sep. 10, 2015

(30) Foreign Application Priority Data

Mar. 6, 2014 (KR) ........................ 10-2014-0026814

(51) Int. Cl.
*A61B 8/00* (2006.01)
*A61B 8/08* (2006.01)
*G01S 7/52* (2006.01)
*A61B 8/14* (2006.01)

(52) U.S. Cl.
CPC ........ *A61B 8/5207* (2013.01); *G01S 7/52033* (2013.01); *G01S 7/52046* (2013.01); *G01S 7/52077* (2013.01); *A61B 8/14* (2013.01); *A61B 8/467* (2013.01)

(58) Field of Classification Search
CPC .......... A61B 8/483; A61B 8/469; A61B 8/485
See application file for complete search history.

(56) References Cited

U.S. PATENT DOCUMENTS

| | | |
|---|---|---|
| 5,993,392 A | 11/1999 | Roundhill et al. |
| 6,666,824 B2 | 12/2003 | Rust et al. |
| 6,743,174 B2 | 6/2004 | Ng et al. |
| 7,833,159 B2 | 11/2010 | Ahn et al. |
| 2010/0305449 A1 | 12/2010 | Wegener et al. |

FOREIGN PATENT DOCUMENTS

| | | |
|---|---|---|
| JP | 2002-172115 A | 6/2002 |
| KR | 10-0748858 B1 | 8/2007 |

*Primary Examiner* — Joseph M Santos Rodriguez
(74) *Attorney, Agent, or Firm* — McDermott Will & Emery LLP

(57) ABSTRACT

A method of generating an ultrasound image includes acquiring a response signal to an ultrasound wave transmitted to an object, changing a level of the acquired response signal depending on a position and an amplitude of the acquired response signal on a scan line, performing logarithmic compression on the level-changed response signal, and generating an ultrasound image based on the compressed signal.

12 Claims, 12 Drawing Sheets

METHOD AND APPARATUS FOR GENERATING ULTRASOUND IMAGE HAVING ENHANCED QUALITY

RELATED APPLICATION

This application claims the benefit of Korean Patent Application No. 10-2014-0026814, filed on Mar. 6, 2014, in the Korean Intellectual Property Office, the disclosure of which is incorporated herein in its entirety by reference.

BACKGROUND

1. Field

One or more embodiments of the present invention relate to a method and apparatus for generating an ultrasound image having enhanced quality.

2. Description of the Related Art

Ultrasound diagnostic apparatuses irradiate an ultrasound signal, generated from a transducer of a probe, onto an object and receive an echo signal reflected from the object, thereby obtaining an image of an internal part of the object. In particular, ultrasound diagnostic apparatuses are used for medical purposes such as observing the inside of an object, detecting a foreign material, and assessing an injury. Ultrasound diagnostic apparatuses have higher stability than diagnostic apparatuses using X-rays, display an image in real time, and are safe because there is no exposure to radioactivity. Thus, they may be widely used along with other image diagnostic apparatuses.

When a related art ultrasound diagnostic apparatus is used, it is necessary to acquire an optimal ultrasound image of a body part to be examined. The ultrasound image should have appropriate sharpness for accurately analyzing the body part. Thus, a user has to finely adjust an image parameter (for example, a time gain compensation (TGC) parameter, a gain parameter, a reject parameter, and a dynamic range (DR) parameter) corresponding to the brightness and contrast of an image to be displayed in order to acquire an optimal ultrasound image. The fine adjustment of the image parameter is not automatically performed by the ultrasound diagnostic apparatus but is manually performed by the user. That is, when the related art ultrasound diagnostic apparatus is used, the user should manually and finely adjust the image parameter through a complicated process in order to improve the quality of a displayed ultrasound image. For this reason, a diagnosis time increases.

SUMMARY

One or more embodiments of the present invention comprises a method and apparatus for generating an ultrasound image having enhanced quality, whereby noise is clearly distinguished from an ultrasound signal for an object through a decompression operation that changes a size of a the ultrasound signal according to an ultrasound response signal and an acquired position on a scan line, thereby generating an ultrasound image having enhanced quality.

Additional aspects will be set forth in part in the description which follows and, in part, will be apparent from the description, or may be learned by practice of the presented embodiments.

According to one or more embodiments of the present invention, a method of generating an ultrasound image by changing a level of a signal on a scan line acquired position and amplitude of an ultrasound response signal depending on an acquired position and amplitude of an ultrasound response signal comprises: acquiring a response signal to an ultrasound wave transmitted to an object; changing a level of the acquired response signal depending on a position and an amplitude of the acquired response signal on a scan line; performing logarithmic compression on the level-changed response signal; and generating an ultrasound image based on the compressed signal.

The changing of the level may be performed by multiplying an amplitude of envelop data, included in the response signal, by a decompression coefficient.

The decompression coefficient may be determined based on at least one of a decompression value, a dynamic range, a minimum detection level of ultrasound signal intensity, and an amplitude of envelop data.

The decompression value may be determined depending on a position of each pixel indicating the ultrasound image.

The decompression value may be preset according to a predetermined reference, or may be set in real time according to a user input.

The decompression coefficient may be determined via the equation below:

$$\alpha(s, z) = 10^{\left\{\left(\frac{DR}{DR-DV(s,z)}-1\right)\cdot(20\cdot\log_{10}(x(s,z))) + \left(1 - \frac{DR}{DR-DV(s,z)}\right)\cdot Min(s,z)\right\}/20}$$

where S denotes a scan line position value, z denotes a depth position value, a(s, z) is a decompression coefficient at coordinates (s, z), DR denotes a dynamic range, DV(s, z) denotes a decompression value at coordinates (s, z), MIN(s, z) denotes a minimum detection level of ultrasound signal amplitude at coordinates (s, z), and x(s, z) denotes an amplitude of envelop data at coordinates (s, z).

According to one or more embodiments of the present invention, an apparatus for generating an ultrasound image by changing a level of a signal on a scan line acquired position and amplitude of an ultrasound response signal depending on an acquired position and amplitude of an ultrasound response signal comprises: a signal acquiring unit that acquires a response signal to an ultrasound wave transmitted to an object; a signal level changing unit that changes a level of the acquired response signal depending on a position and an amplitude of the acquired response signal on a scan line; a signal compressing unit that performs logarithmic compression on the level-changed response signal; and an ultrasound image generating unit that generate an ultrasound image based on the compressed signal.

The signal level changing unit may change the level of the response signal by multiplying an amplitude of envelop data included in the response signal by a decompression coefficient.

The decompression coefficient may be determined based on at least one of a decompression value, a dynamic range, a minimum detection level of ultrasound signal intensity, and an amplitude of envelop data.

The decompression value may be determined depending on a position of each pixel indicating the ultrasound image.

The decompression value may be preset according to a predetermined reference, or is set in real time according to a user input.

The decompression coefficient may be determined via the equation below:

$$\alpha(s, z) = 10^{\left\{\left(\frac{DR}{DR-DV(s,z)}-1\right)\cdot(20\cdot\log_{10}(x(s,z))) + \left(1 - \frac{DR}{DR-DV(s,z)}\right)\cdot Min(s,z)\right\}/20}$$

where S denotes a scan line position value, z denotes a depth position value, a(s, z) is a decompression coefficient at coordinates (s, z), DR denotes a dynamic range, DV(s, z) denotes a decompression value at coordinates (s, z), MIN(s, z) denotes a minimum detection level of ultrasound signal amplitude at coordinates (s, z) coordinates, and x(s, z) denotes an amplitude of envelop data at coordinates (s, z).

According to one or more embodiments of the present invention, provided is a non-transitory computer-readable storage medium storing a program for executing the above method in a computer.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1A:
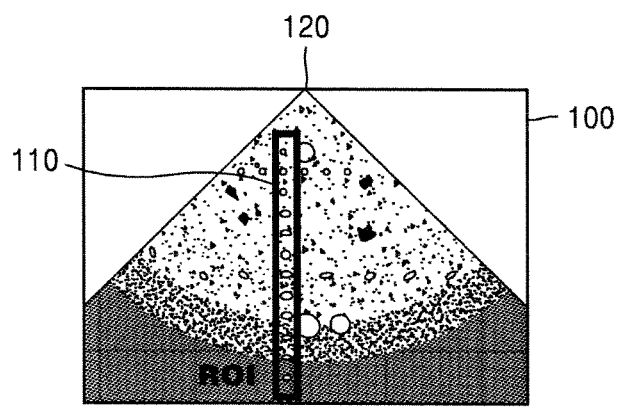
FIG. 1A is a diagram illustrating an ultrasound image generated in the related art.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list.

The advantages, features, and aspects of the present invention will become apparent from the following description of the embodiments with reference to the accompanying drawings, which is set forth hereinafter. The present invention may, however, be embodied in different forms and should not be construed as limited to the embodiments set forth herein. Rather, these embodiments are provided so that this disclosure will be thorough and complete, and will fully convey the scope of the present invention to those of ordinary skill in the art. Like reference numerals refer to like elements throughout.

In this disclosure below, when it is described that one component comprises (or includes or has) some elements, it should be understood that the component may comprise (or include or has) only those elements or may comprise (or include or have) other elements if there is no specific limitation. The term "module", as used herein, means, but is not limited to, a software or hardware component, such as a Field Programmable Gate Array (FPGA) or an Application Specific Integrated Circuit (ASIC), which performs certain tasks. A module may advantageously be configured to reside in the addressable storage medium and configured to execute on one or more processors. Thus, a module may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for in the components and modules may be combined into fewer components and modules or further separated into additional components and modules.

Exemplary embodiments of the present invention capable of being easily embodied by those of ordinary skill in the art will now be described in detail with reference to the accompanying drawings. The present invention may, however, be embodied in many different forms and should not be construed as being limited to the embodiments set forth herein. In the accompanying drawings, a portion irrelevant to a description of the present invention will be omitted for clarity.

Terms used in the present invention have been selected as general terms which are widely used at present, in consideration of the functions of the present invention, but may be altered according to the intent of an operator of ordinary skill in the art, conventional practice, or introduction of new technology. Also, if there is a term which is arbitrarily selected by the applicant in a specific case, a meaning of the term will be described in detail in a corresponding description portion of the present invention. Therefore, the terms should be defined on the basis of the entire content of this specification instead of a simple name of each of the terms.

Terms used herein will be briefly described, and the present invention will be described in detail.

The term "ultrasound image" used herein denotes an image of an object acquired by using an ultrasound wave. Also, the term "object" used herein may include a person, an animal, a part of the person, or a part of the animal. For example, an object may include an organ such as a liver, a heart, a womb, a brain, breasts, an abdomen, or the like, or a blood vessel. Also, the term "object" may include a phantom. The phantom denotes a material having a volume that is very close to a density and effective atomic number of an organism, and may be a spherical phantom having a characteristic similar to a physical body.

Moreover, the term "user" used herein is a medical expert, and may be a medical doctor, a nurse, a medical technologist, a medical image expert, or the like, or may be an engineer who repairs medical apparatuses. However, the user is not limited thereto.

Hereinafter, embodiments of the present invention will be described in detail with reference to the accompanying drawings.

FIG. 1A is a diagram illustrating an ultrasound image 100. Referring to FIG. 1A, a user's region of interest (ROI) 110 may be set in the ultrasound image 100. In the ultrasound image 100, a vertex 120 of a fan-shaped area is a portion where an ultrasound probe is located. At the vertex 120 of the ultrasound image 100, a depth with respect to the ultrasound probe is 0, and the depth becomes deeper progressively farther away from the vertex 120. A level of an ultrasound signal reflected at a faraway position from the vertex 120 is less than that of an ultrasound signal reflected at a relatively close position from the vertex 120. An ultrasound signal at a deeper depth is an ultrasound signal reflected from a faraway position, and thus, a level of the ultrasound signal is gradually reduced.

Figure 1B:
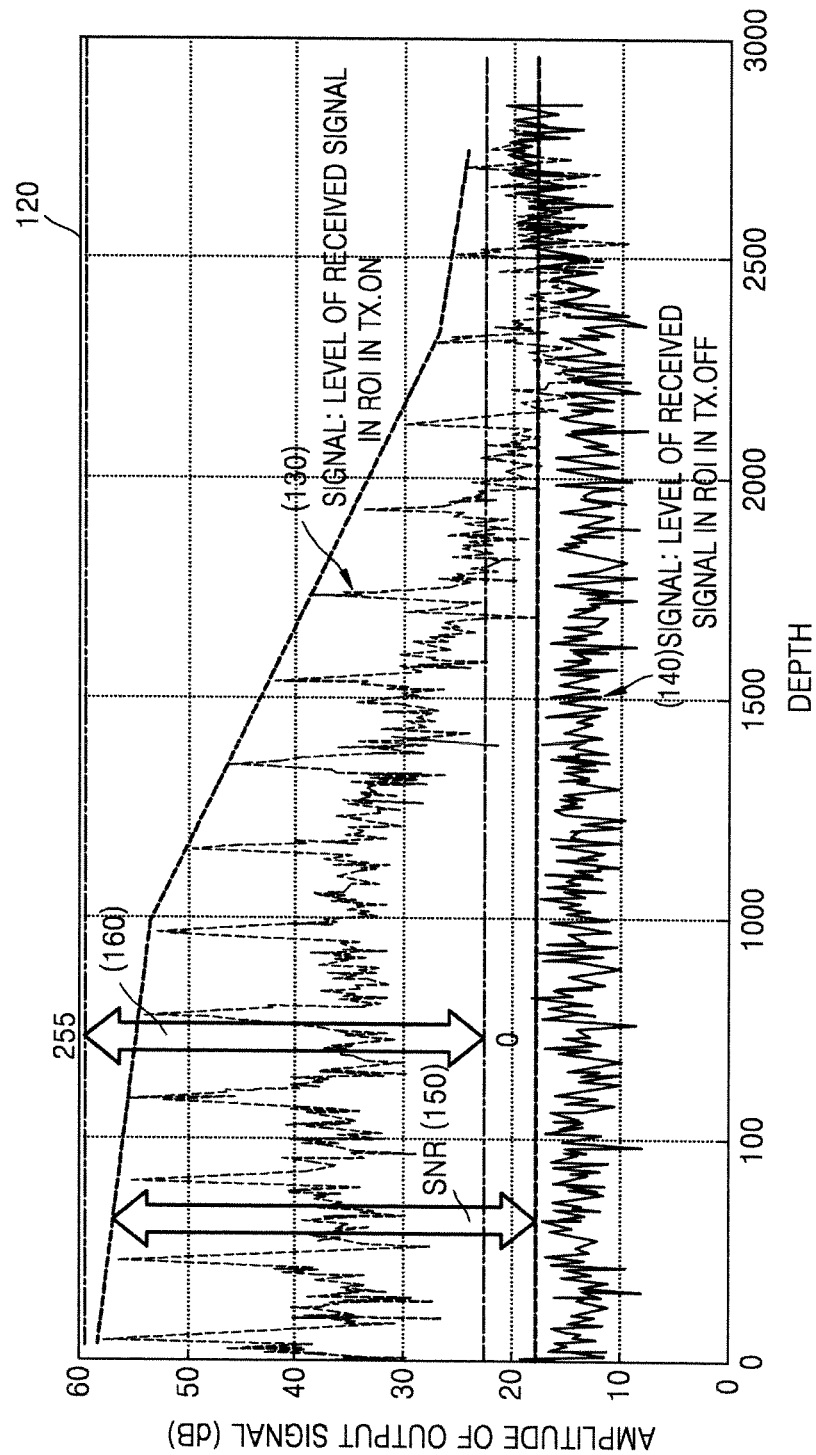
FIG. 1B is a diagram illustrating an ultrasound signal generated by using an analog time gain compensation (ATGC) method.

FIG. 1B is a diagram illustrating an ultrasound signal generated by using an analog time gain compensation (ATGC) method. FIG. 1B is a graph 120 for comparing an amplitude of an ultrasound output signal 130 based on a depth in the user's ROI 110 of the ultrasound image 100 of FIG. 1A. Referring to the graph 120, the amplitude of the ultrasound output signal 130 is reduced as a depth becomes deeper from 0. The amplitude of the ultrasound output signal 120 is classified into 256 levels from 0 to 255. A level 0 is a level where the amplitude of the ultrasound output signal 120 is the lowest, and a level 225 is a level where the amplitude of the ultrasound output signal 120 is the highest. A dynamic range (DR) 160 may include a level 0 to a level 255 for classifying the 255 of the ultrasound output signal 120.

Noise 140 may include white noise which is generated in an ultrasound diagnostic apparatus. A signal-to-noise ratio (SNR) 150 denotes a decibel count when signal power exceeds noise power. The SNR 150 denotes an energy ratio of a signal and noise. The SNR 150 of FIG. 1B denotes an energy ratio of power of the ultrasound output signal 130 and power of the noise 140. When a value of the SNR 150 is large, a level of the ultrasound output signal 130 is higher than that of the noise 140, and thus, the ultrasound output signal 130 is clearly distinguished. However, when the value of the SNR 150 is small, it is difficult to distinguish the noise 140 and the ultrasound output signal 130. Therefore, an ultrasound image generated based on the ultrasound output signal 130 is not shown with proper sharpness. Since the amplitude of the ultrasound output signal 130 is inversely proportional to depth, the amplitude of the ultrasound output signal 130 is reduced as the depth increases. However, since noise generally occurs in an apparatus, there is approximately no correlation between a depth of the ultrasound probe and the amplitude of the noise. In a section where the depth is shallow, since the amplitude of the ultrasound output signal 130 is large, the SNR 150 is high, but as the depth increases, the SNR 150 becomes lower, and thus, it is not possible to distinguish the ultrasound output signal 130 and the noise 140. Referring to FIG. 1B, the ultrasound output signal 130 and the noise 140 are compensated for through an ATGC operation in order to enlarge a portion where the ultrasound output signal 130 and the noise 140 are not distinguished at a large depth. However, as the depth increases, the SNR 150 is rapidly reduced, an attenuation of the ultrasound output signal 130 exceeds a compensation range based on the ATGC operation, and thus, in a section where the depth is large (for example, a section in which a sample value of the depth is 2,500 to 3,000 units), it is difficult to distinguish the ultrasound output signal 130 because the amplitude of the ultrasound output signal 130 is similar to that of the noise 140.

Figure 1C:
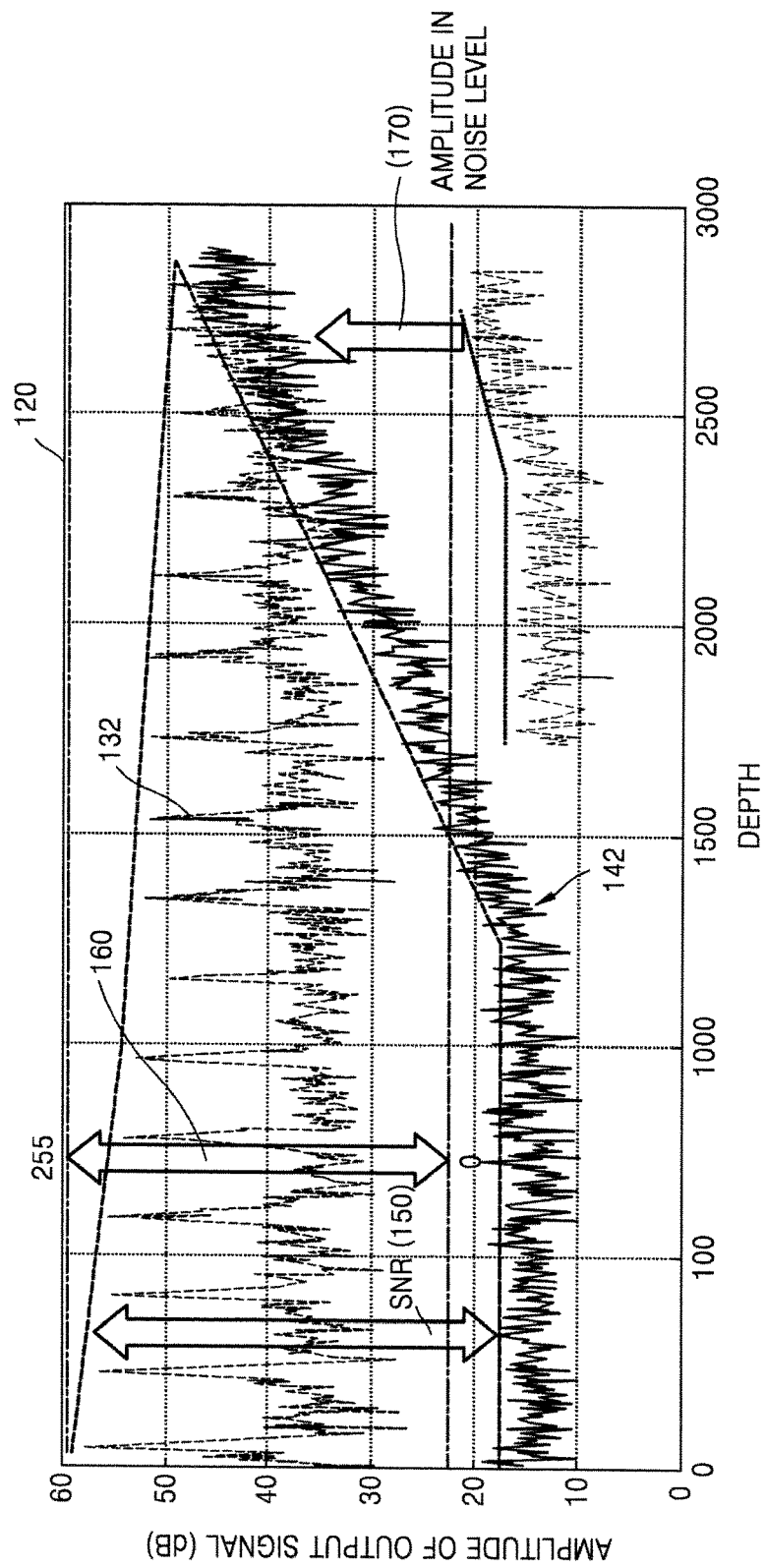
FIG. 1C is a diagram illustrating an ultrasound signal generated by using a digital time gain compensation (DTGC) method.

FIG. 1C is a diagram illustrating an ultrasound signal which is generated by using a digital time gain compensation (DTGC) method. FIG. 1C is a graph 120 for comparing an amplitude of an ultrasound output signal 132 based on a depth in the user's ROI 110 of the ultrasound image 100 of FIG. 1A. Referring to FIG. 1C, the ultrasound output signal 132 and noise 142 are compensated for through a DTGC in order to enlarge a portion where the ultrasound output signal 132 and the noise 142 are not distinguished at a large depth. A degree of attenuation of the ultrasound output signal 132 which is obtained through the DTGC operation is reduced, but all signals including the noise 142 are compensated for. Therefore, a noise level also increases (as shown by 170), and thus, a difference between the ultrasound output signal 132 and noise 142 is reduced.

Figure 1D:
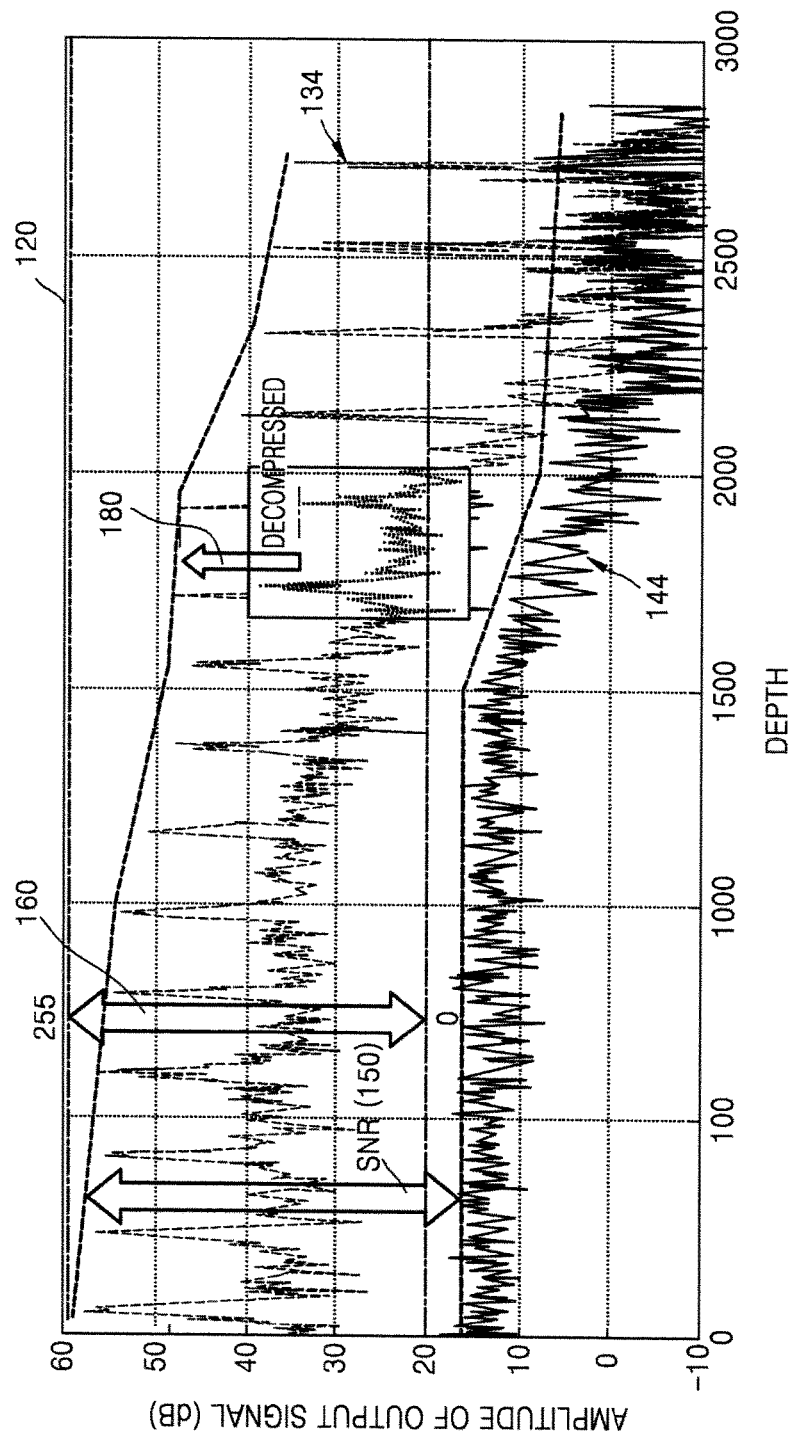
FIG. 1D is a diagram illustrating an ultrasound signal generated according to an embodiment of the present invention.

FIG. 1D is a diagram illustrating an ultrasound signal generated according to an embodiment of the present invention. FIG. 1D is a graph 120 that shows an amplitude of an ultrasound output signal 134 based on a depth in the user's ROI 110 of the ultrasound image 100 of FIG. 1A. Referring to the graph 120, the amplitude of the ultrasound output signal 134 is reduced as a depth increases from 0. Referring to FIG. 1D, an operation of changing a level of the ultrasound output signal 134 may be performed for supplementing that it is difficult to distinguish the ultrasound output signal 134 and noise 144 as the depth increases. The level changing operation may be referred to as a decompression operation 180. Comparing a signal obtained through the decompression operation 180 of FIG. 1D with the signal 130 obtained through the ATGC operation of FIG. 1B and the signal 132 obtained through the DTGC operation of FIG. 1C, it may be seen that although the ultrasound output signal 134 becomes deeper through the decompression operation 180, it is difficult to distinguish the noise 144 and the ultrasound output signal 134 in a corresponding portion, and the amplitude of the ultrasound output signal is large.

Figure 10:
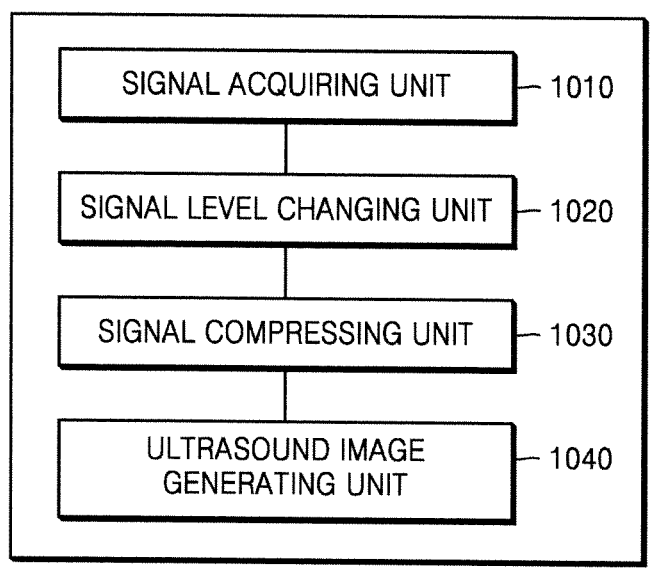
FIG. 10 is a block diagram illustrating an ultrasound image generating apparatus according to an embodiment of the present invention.

FIG. 10 is a block diagram illustrating an ultrasound image generating apparatus 1000 according to an embodiment of the present invention. The ultrasound image generating apparatus 1000 according to an embodiment of the present invention may include a signal acquiring unit 1010, a signal level changing unit 1020, a signal compressing unit 1030, and an ultrasound image generating unit 1040. Operations of the components 1010, 1020, 1030 and 1040 of the ultrasound image generating apparatus 1000 will be described in detail with reference to FIG. 2.

Figure 2:
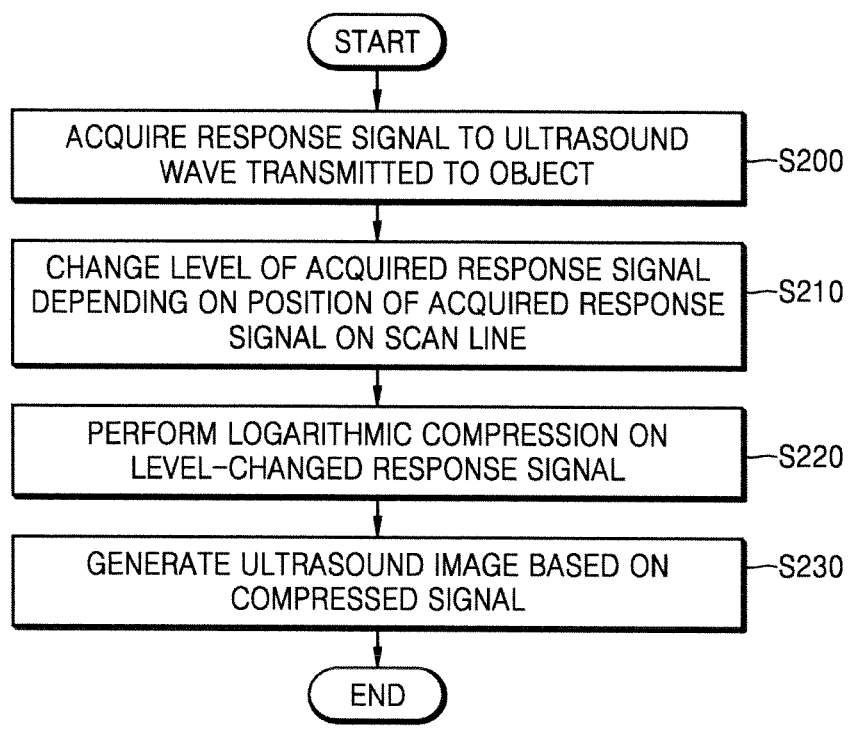
FIG. 2 is a flowchart illustrating an ultrasound image generating method according to an embodiment of the present invention.

FIG. 2 is a flowchart illustrating an ultrasound image generating method according to an embodiment of the present invention.

In operation S200, the signal acquiring unit 1010 may acquire a response signal to an ultrasound wave which is transmitted to an object.

In operation S210, the signal level changing unit 1020 may change a level of the acquired response signal depending on a position and an amplitude of the acquired response signal on a scan line. The level of the response signal may be changed by multiplying an amplitude of envelop data included in the response signal by a decompression coefficient. The decompression coefficient may be determined based on at least one of a decompression value "DV", as dynamic range "DR", a minimum detection level "MIN(s, z)" of ultrasound signal amplitude, and an amplitude of envelop data. The decompression value "DR" and the minimum detection level "MIN(s, z)" of the ultrasound signal amplitude may be determined depending on a position of each pixel indicating an ultrasound image. The decompression value "DR" may be preset based on a predetermined reference, or may be set in real time according to a user input. The decompression value "DR" may be determined via the following Equation (1):

$$\alpha(s, z) = 10^{\{(\frac{DR}{DR-DV(s,z)}-1)(20 \cdot \log_{10}(x(s,z))) + (1 - \frac{DR}{DR-DV(s,z)}) \cdot Min(s,z)\}/20} \quad (1)$$

where S denotes a scan line position value, z denotes a depth position value, a(s, z) is a decompression coefficient at coordinates (s, z), DR denotes a dynamic range, DV(s, z) denotes a decompression value at coordinates (s, z), MIN(s, z) denotes a minimum detection level of ultrasound signal intensity at coordinates (s, z) coordinates, and x(s, z) denotes an amplitude of envelop data at coordinates (s, z).

In operation S220, the signal compressing unit 1030 may perform logarithmic compression on the level-changed response signal. The ultrasound image generating apparatus 1000 may perform the logarithmic compression of the response signal to convert the response signal into data which is used to generate an ultrasound image.

In operation S230, the ultrasound image generating unit 1040 may generate the ultrasound image on the basis of the compressed signal.

Figure 3:
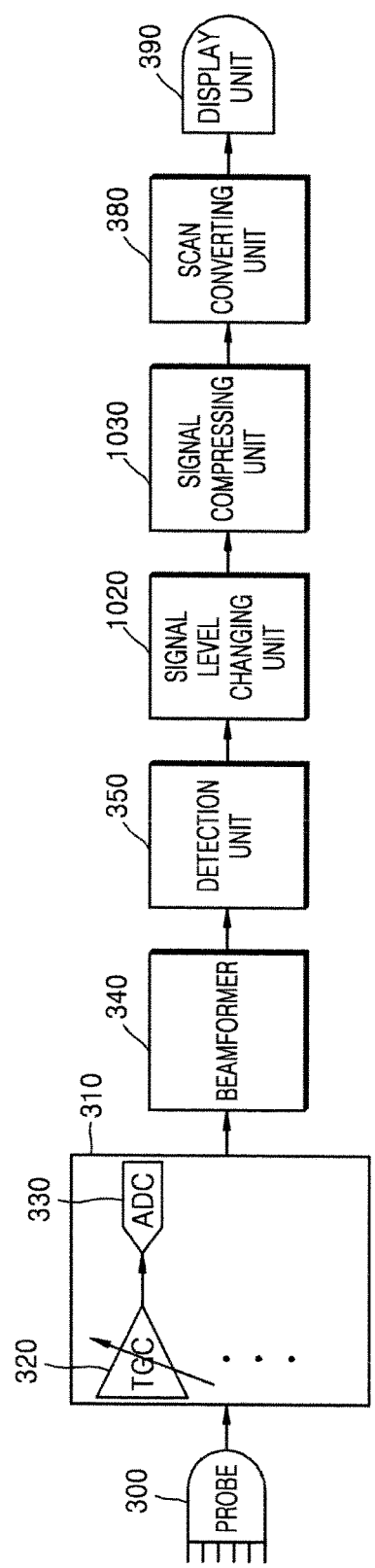
FIG. 3 is a conceptual diagram schematically illustrating an ultrasound image generating apparatus according to an embodiment of the present invention.

FIG. 3 is a conceptual diagram schematically illustrating an ultrasound image generating apparatus 1000 according to an embodiment of the present invention.

The ultrasound image generating apparatus 1000 according to an embodiment of the present invention may include a probe 300, a signal converting unit 310, a beamformer 340, a detection unit 350, a signal level changing unit 1020, a signal compressing unit 1030, a scan converting unit 380, and a display unit 390.

The probe 300 may transmit an ultrasound signal to an object, and receive an echo signal reflected from the object. The probe 300 may include a plurality of transducers, and each of the plurality of transducers may vibrate according to an electrical signal applied thereto to generate an ultrasound wave that is sound energy. Also, the probe 300 may be wiredly or wirelessly connected to a body of the ultrasound image generating apparatus 1000, which may include a plurality of the probes 300 depending on an implementation type.

The signal converting unit 310 may logarithmically amplify the echo signal, which is received by the probe 300 through a time gain compensation (TGC) unit 320, to enhance an amplitude of the echo signal. The signal converting unit 310 may convert the echo signal, which is an analog signal, into a digital signal by using an analog-to-digital converter (ADC) 330.

The beamformer 340 may perform beamforming of the echo signal. The beamforming denotes an operation of electronically focusing an ultrasound wave. For example, when focusing delay varies with time, the beamformer 340 may gradually move a focusing point for all points on a scan line and focus the echo signal.

The detection unit 350 may detect and acquire the beamformed echo signal by using an ultrasound sensor. In the present specification, for convenience of description, the acquired echo signal is a response signal.

The signal level changing unit 1020 may change a level of the acquired response signal depending on a position and an amplitude of the acquired response signal on the scan line. The signal level changing unit 1020 may perform an operation including the operation which has been described above in operation S210 of FIG. 2.

The signal compressing unit 1030 may perform logarithmic compression of the size-changed response signal. The signal compressing unit 1030 may perform an operation including the operation which has been described above in operation S220 of FIG. 2.

The scan converting unit 380 may perform scan conversion of the compressed response signal. The scan conversion may be referred to as rasterization, and may include an operation in which a graphics object to be displayed is expressed as a set of discrete pixel values. The scan conversion may include an operation in which the graphics object is displayed as pixel information having a two-dimensional (2D) matrix type having X and Y coordinate values. In the present specification, the scan conversion may include an operation of converting the compressed response signal into an ultrasound image.

The display unit 390 may display the converted ultrasound image.

Figure 4:
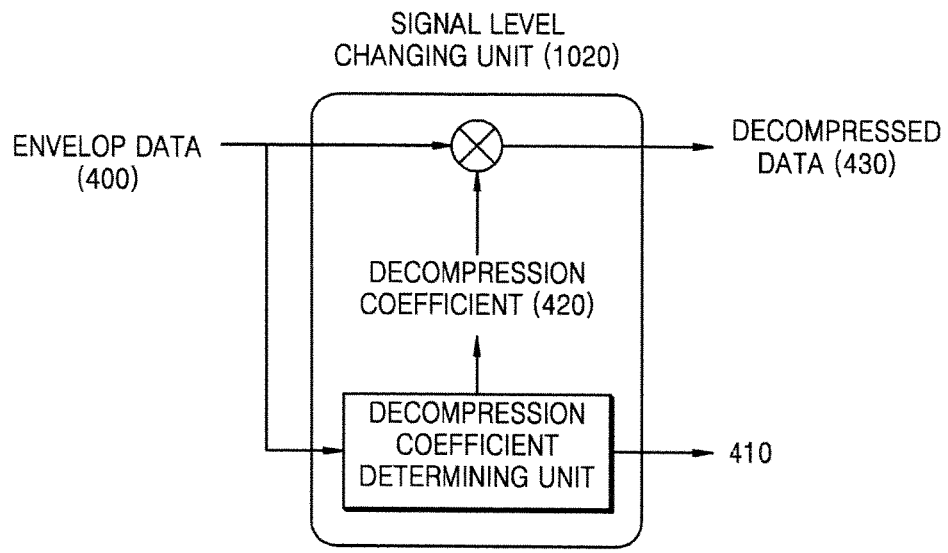
FIG. 4 is a diagram for describing a signal level changing unit according to an embodiment of the present invention.

FIG. 4 is a diagram for describing the signal level changing unit 1020 according to an embodiment of the present invention.

Referring to FIG. 4, amplitude of envelop data 400 may include the response signal which is acquired by using the detection unit 350 of FIG. 3. In other words, the signal level changing unit 1020 may receive the amplitude of envelop data 400. The signal level changing unit 1020 may include a decompression coefficient determining unit 410. In the signal level changing unit 1020, the decompression coefficient determining unit 410 may determine a decompression coefficient 420 by using the received amplitude of envelop data 400. The signal level changing unit 1020 may multiply the received amplitude of envelop data 400 and the determined decompression coefficient 420 to output size-changed data, for example, decompressed data 430.

Figure 5:
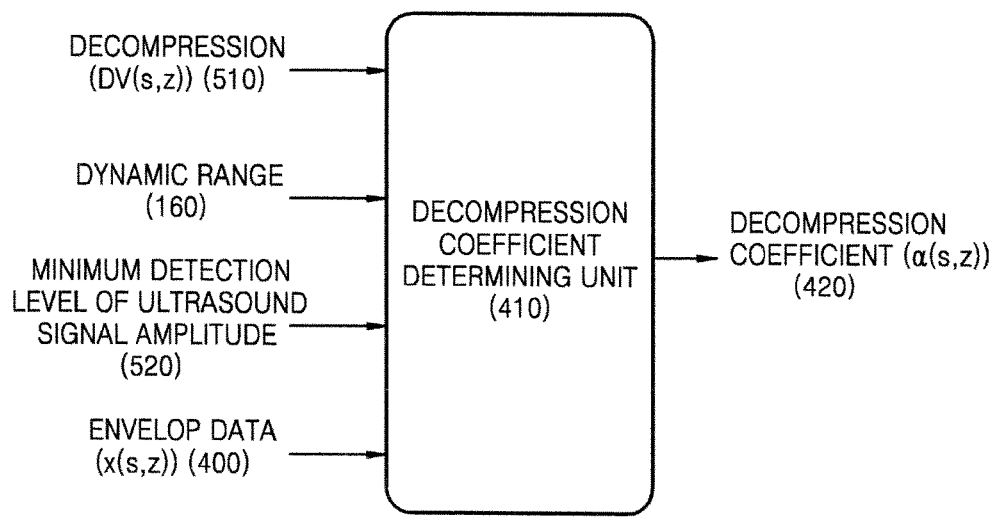
FIG. 5 is a diagram for describing a decompression coefficient determining unit according to an embodiment of the present invention.

FIG. 5 is a diagram for describing a decompression coefficient determining unit 410 according to an embodiment of the present invention.

Referring to FIG. 5, the decompression coefficient determining unit 410 may be included in the signal level changing unit 1020 of FIG. 4. The decompression coefficient determining unit 410 may receive a decompression value "DV" 510, aa dynamic range "DR" 160, a minimum detection level "MIN(s, z)" 520 of ultrasound signal intensity, and an amplitude of envelop data "X(s, z)" 400 to determine a decompression coefficient "a(s, z)".

The decompression value 510 may include a value indicating a degree of decompression which is performed a scan line and a depth on the scan line. The dynamic range 160 denotes a range in which an ultrasound signal can be acquired and is determined by using a compression curve. The minimum detection level 520 of the ultrasound signal amplitude may include a 0 level, which is the lowest level among all levels of an ultrasound signal for classifying ultrasound signals. The amplitude of envelop data 400 may include a response signal acquired by the detection unit 350.

An embodiment of a method of determining a decompression coefficient will be described below with reference to FIG. 9.

Figure 6A:
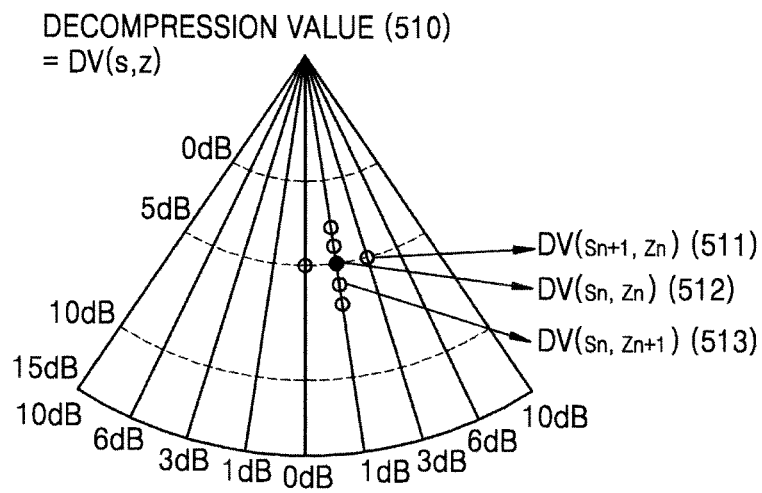
FIGS. 6A and 6B are diagrams for describing an influence of a change in a decompression value according to an embodiment of the present invention.
Figure 6B:
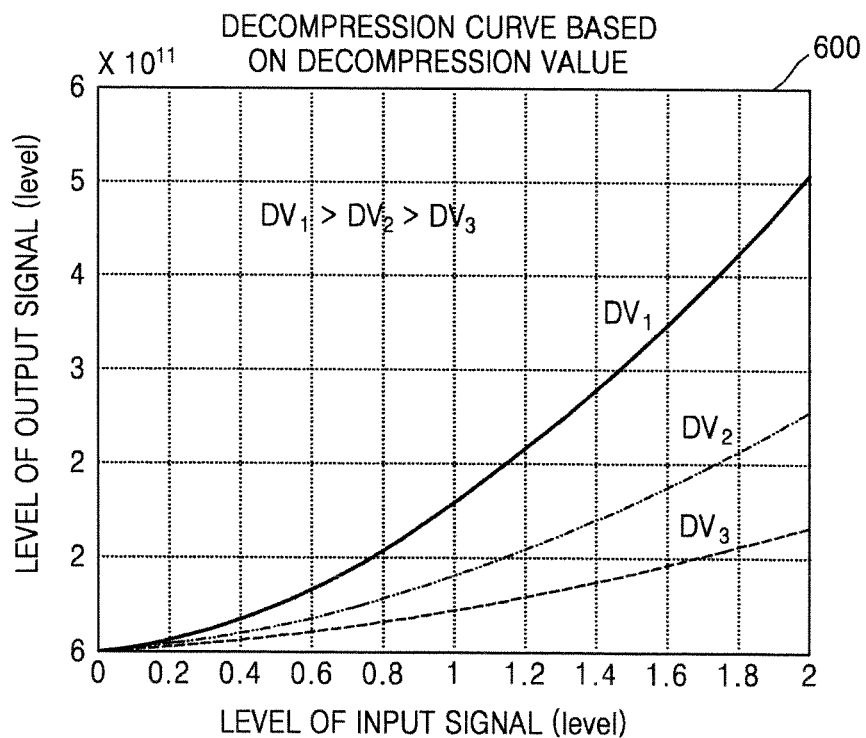

FIGS. 6A and 6B are diagrams for describing an influence of a change in a decompression value according to an embodiment of the present invention.

Referring to FIG. 6A, the decompression value 510 may have different coordinate values depending on a scan line and a depth on the scan line. For example, points P1 and P2 are points which have the same depth but have different scan lines, and may have different decompression values "DV (Sn+1,Zn)" 511 and "DV(Sn,Zn)" 512. Also, the point P2 and a point P3 are points which have the same scan line but have different depths, and may have different decompression values "DV(Sn,Zn)" 512 and "DV(Sn,Zn+1)" 513. The decompression value 510 based on each scan line and a depth may be preset according to a reference (for example, a higher decompression value than a decompression value based on a different depth is applied in a section where a sample value of a depth is 1,500 to 2,000 units), and may be arbitrarily changed by a user.

Referring to FIG. 6B, it may be seen that levels of a plurality of the decompression values 510 differ "DV1>DV2>DV3". In a decompression curve 600 based on the decompression values 510, it may be seen that as a decompression value increases, a level of an output signal based on a level of an input signal becomes higher.

Figure 7A:
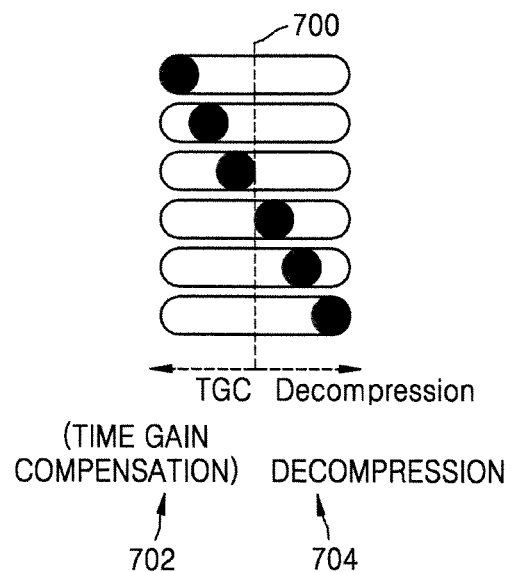
FIGS. 7A and 7B are diagrams for describing a method of generating an ultrasound image by changing a decompression value according to an embodiment of the present invention.
Figure 7B:
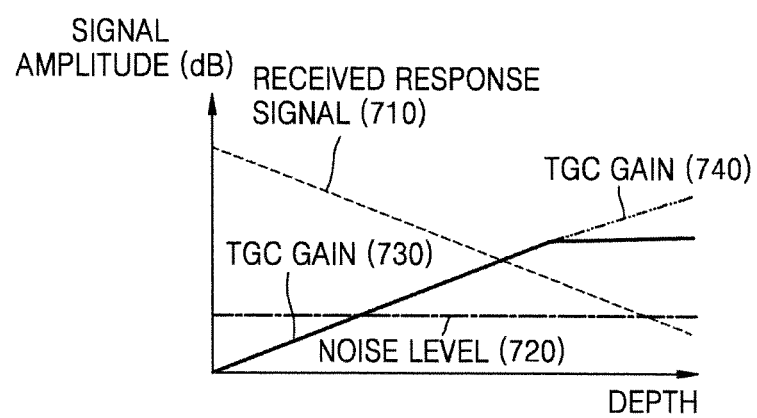

FIGS. 7A and 7B are diagrams for describing a method of generating an ultrasound image by changing a decompression value according to an embodiment of the present invention.

Referring to FIG. 7A, an ultrasound image may be generated by changing a decompression value by using a switch 700. The decompression value 510 may be preset according to a predetermined reference, or may be set in real time according to a user input. For example, a depth of the ultrasound image may be divided into six sections so as to change the decompression value, and the decompression value 510 in each of the six sections may be set previously or in real time. When a user moves six switches in each section to the right by using the switch 700 or a virtual switch so as to change the decompression value as illustrated in FIG. 7A, a time gain value increases in a time gain compensation 702 section, and a decompression 704 value is fixed. Also, when the user moves the six switches in each section to the right above the time gain compensation section and a decompression region so as to change the decompression value, the time gain compensation 702 is fixed to the maximum value, and since the decompression 704 increases, the decompression value 510 may be set to a high value.

The above-described switch 700 may be included in a control panel of an ultrasound diagnostic apparatus. Also, the above-described virtual switch may be displayed as a graphics user interface (GUI) on a display unit, and may be manipulated by the user.

A relationship between a TGC gain 730 and a decompression gain 740 will now be described for a received response signal 710 and a noise level 720 with reference to FIG. 7B.

The received response signal 710 may have lower amplitude as a depth increases. The noise level 720 denotes an amplitude of noise which occurs in an apparatus and may have certain intensity irrespective of a depth. In the TGC gain 730, as a depth becomes deeper, a higher gain is given to the received response signal 710, but in a certain depth or more, a constant gain may be given to the received response signal 710. In the decompression gain 740, as a depth becomes deeper, a higher gain may be given to the received response signal 710, even in a case of a certain depth or more in which a constant gain is given in the TGC gain 730. Therefore, a user compensates for the received response signal 710 by further using the decompression gain 740 instead of using only the TGC gain 730, and thus, it is easy to distinguish the received response signal 710 from noise.

Figure 8:
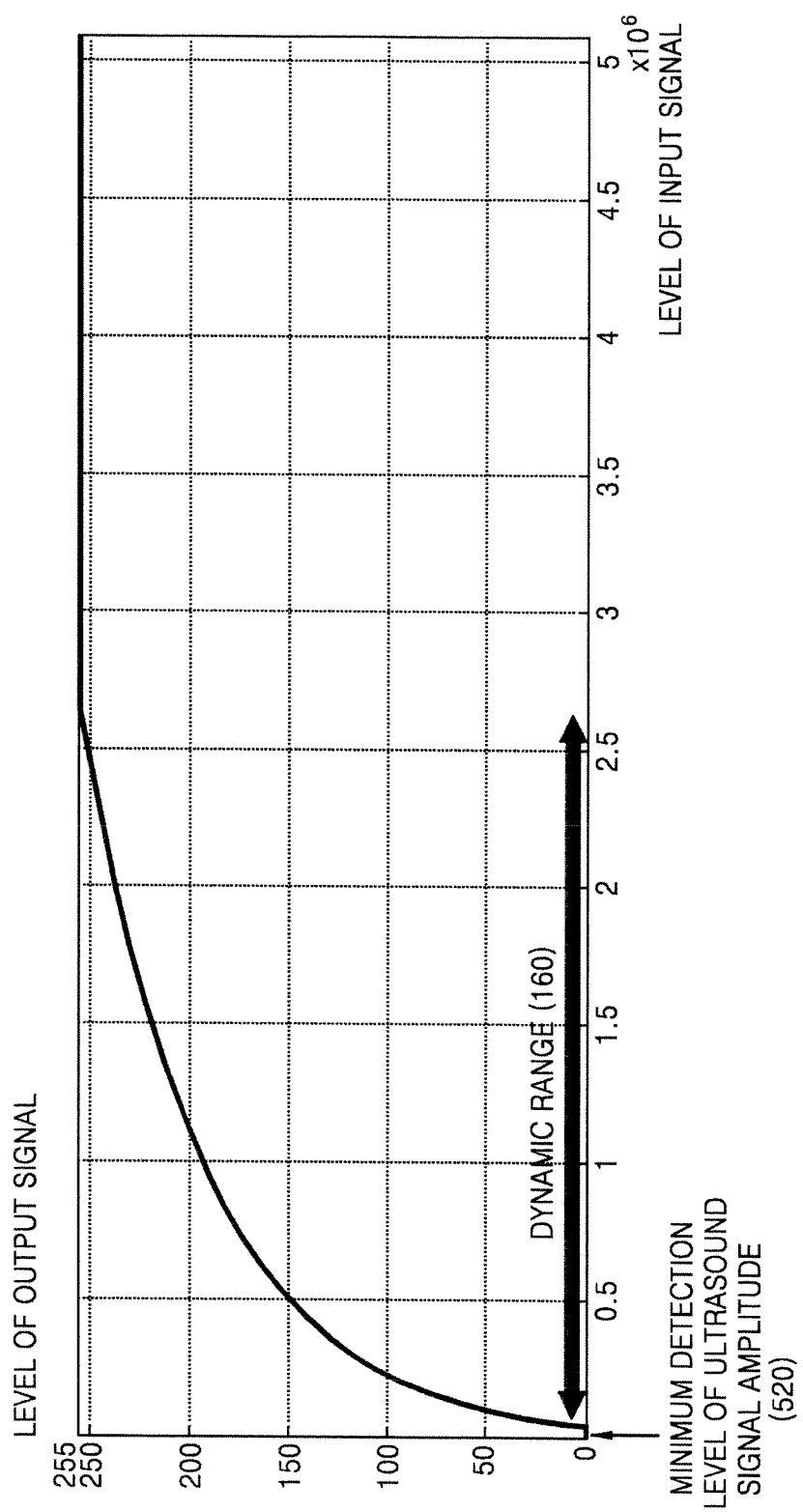
FIG. 8 is a diagram for describing a decompression coefficient determining method according to an embodiment of the present invention.

FIG. 8 is a diagram for describing a decompression coefficient determining method according to an embodiment of the present invention. FIG. 8 shows a compression curve, and the ultrasound image generating apparatus 1000 may calculate a dynamic range 160 and a minimum detection level 520 of ultrasound signal intensity by using information which is shown in the compression curve. The ultrasound detection range 160 may include a range in which the ultrasound image generating apparatus 1000 is capable of acquiring an ultrasound signal. The ultrasound image generating apparatus 1000 may classify the ultrasound signal by level when acquiring the ultrasound signal, and the minimum detection level 520 of the ultrasound signal intensity may include a 0 level that is the lowest level. The ultrasound image generating apparatus 1000 may use, as inputs of the decompression coefficient determining unit 410, the ultrasound detection range 160 and the minimum detection level 520 of the ultrasound signal intensity by using the compression curve.

Figure 9:
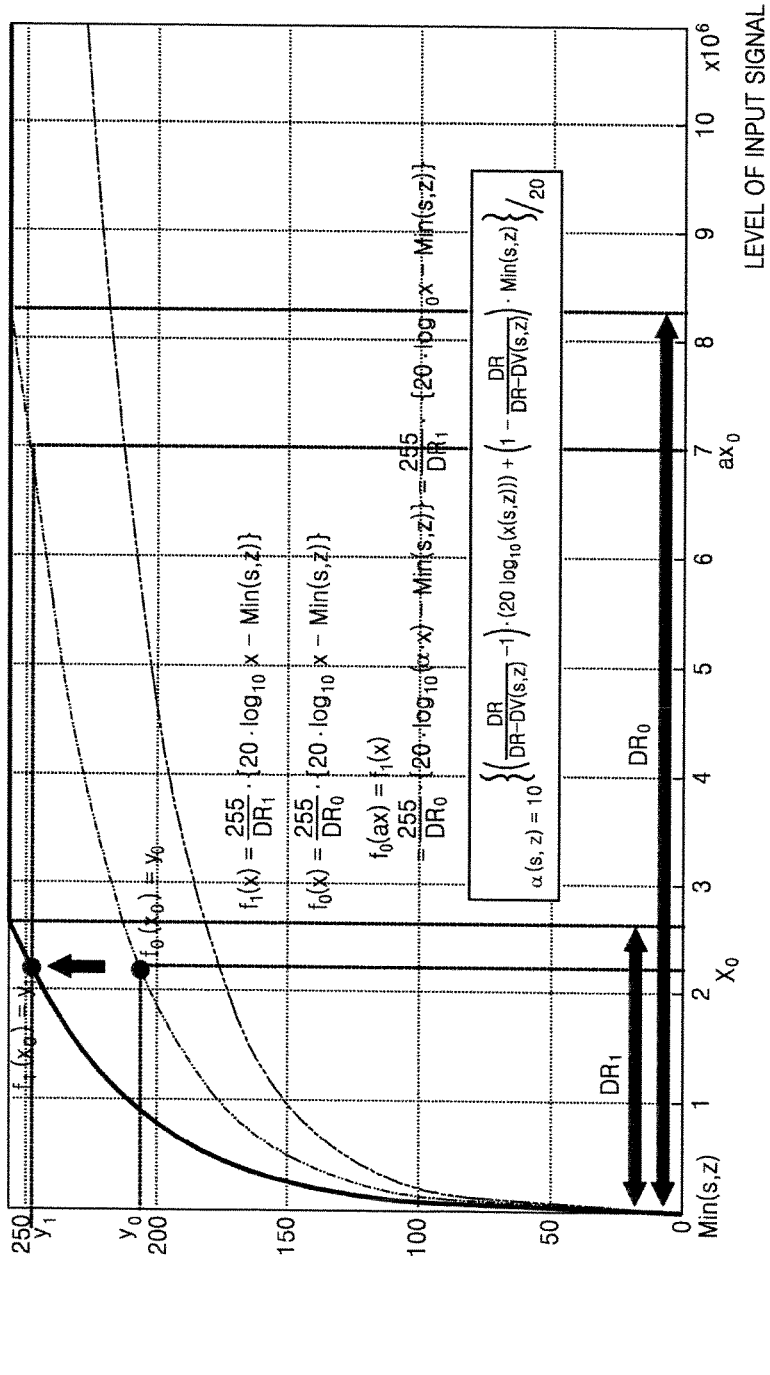
FIG. 9 is a diagram for describing a decompression coefficient determining method according to another embodiment of the present invention.

FIG. 9 is a diagram for describing a decompression coefficient determining method according to another embodiment of the present invention.

FIG. 9 is a diagram illustrating an operation of determining a decompression coefficient by using input values input to the decompression coefficient determining unit 410. The decompression coefficient may be determined via Equation (1).

Referring to FIG. 9, the decompression coefficient may be determined by using a relationship between f0(x) and f1(x). Thus, the decompression coefficient is calculated by using the following equations.

$$f_1(x) = \frac{255}{DR_1} \cdot \{20 \cdot \log_{10} x - \mathrm{MIN}(s, z)\}$$

$$f_0(x) = \frac{255}{DR_0} \cdot \{20 \cdot \log_{10} x - \mathrm{MIN}(s, z)\}$$

$$f_0(\alpha x) = f_1(x)$$

$$\frac{255}{DR_0} \cdot \{20 \cdot \log_{10}(\alpha \cdot x) - \mathrm{MIN}(s, z)\} = \frac{255}{DR_1} \cdot \{20 \cdot \log_{10} x - \mathrm{MIN}(s, z)\}$$

$$\alpha(s, z) = 10^{\left[\left(\frac{DR}{DR-DV(s,z)}-1\right)\cdot(20\cdot\log_{10}(x(s,z)))+\left(1-\frac{DR}{DR-DV(s,z)}\right)\cdot Min(s,z)\right]/20}$$

where DR0-DR1 denotes DV(s, z), that is, a decompression value, DR in the calculated decompression coefficient is equal to DR0. DR-DV(s, z) is DR0-DV(s, z), and is equal to DR1.

In the above equations, S denotes a scan line position value, z denotes a depth position value, a(s, z) is a decompression coefficient at coordinates (s, z), DR denotes an dynamic range, DV(s, z) denotes a decompression value at coordinates (s, z), MIN(s, z) denotes a minimum detection level of ultrasound signal amplitude at coordinates (s, z), and x(s, z) denotes an amplitude of envelop data at coordinates (s, z).

FIG. 10 is a block diagram illustrating the ultrasound image generating apparatus 1000 according to an embodiment of the present invention. The ultrasound image generating apparatus 1000 according to an embodiment of the present invention may include the signal acquiring unit 1010, the signal level changing unit 1020, the signal compressing unit 1030, and the ultrasound image generating unit 1040.

The signal acquiring unit 1010 may acquire a response signal to an ultrasound wave which is transmitted to an object. The signal acquiring unit 1010 may include the probe 300, signal converting unit 310, beamformer 340, and detection unit 350 of FIG. 3.

The signal level changing unit 1020 may change a level of the acquired response signal depending on a position and an amplitude of the acquired response signal on a scan line. The signal level changing unit 1020 may be change the level of the response signal multiplying an amplitude of envelop data, included in the response signal, by a decompression coefficient. The decompression coefficient may be determined based on at least one of a decompression value "DV", a dynamic range "DR", a minimum detection level "MIN(s, z)" of ultrasound signal intensity, and an amplitude of envelop data. The decompression value "DR" and the minimum detection level "MIN(s, z)" of the ultrasound signal intensity may be determined depending on a position of each pixel indicating an ultrasound image. The decompression value "DR" may be preset based on a predetermined reference, or may be set in real time according to a user input. The decompression value "DR" may be determined as expressed in the following Equation:

$$\alpha(s, z) = 10^{\{(\frac{DR}{DR-DV(s,z)}-1)\cdot(20\cdot\log_{10}(x(s,z)))+(1-\frac{DR}{DR-DV(s,z)})\cdot Min(s,z)\}/20}$$

where S denotes a scan line position value, z denotes a depth position value, a(s, z) is a decompression coefficient by (s, z) coordinates, DR denotes a dynamic range, DV(s, z) denotes a decompression value by (s, z) coordinates, MIN(s, z) denotes a minimum detection level of ultrasound signal intensity by (s, z) coordinates, and x(s, z) denotes an amplitude of envelop data by (s, z) coordinates.

The signal compressing unit 1030 may perform logarithmic compression of the size-changed response signal.

The ultrasound image generating unit 1040 may generate an ultrasound image on the basis of a compressed signal. The ultrasound image generating unit 1040 may include the scan converting unit 380 and display unit 390 of FIG. 3. The scan converting unit 380 may generate the ultrasound image through a scan conversion operation. The display unit 390 may display the generated ultrasound image. The ultrasound image may include a Doppler image which expresses a moving object by using the Doppler effect, in addition to a grayscale image which is acquired by scanning an object in an amplitude (A) mode, a brightness (B) mode, and a motion (M) mode. The Doppler image may include a blood Doppler image (or called a color Doppler image) indicating a flow of blood, a tissue Doppler image indicating a motion of a tissue, and a spectral Doppler image that displays a moving speed of the target object as a waveform.

The ultrasound image generating apparatus 1000 may extract a B mode component from ultrasound data, and process the B mode component. The ultrasound image generating apparatus 1000 may generate an ultrasound image in which intensity of a signal is expressed as brightness, based on the extracted B mode component.

The ultrasound image generating apparatus 1000 may perform a volume rendering operation on volume data to generate a three-dimensional (3D) ultrasound image, and generate an elastic image in which a degree of change of an object due to a pressure is expressed as an image. The ultrasound image generating apparatus 1000 may express, as a text and graphics, various pieces of additional information on the ultrasound image. The generated ultrasound image may be stored in a memory.

The display unit 390 may display the generated ultrasound image. The display unit 390 may display various pieces of information associated with an ultrasound diagnosis, in addition to the ultrasound image, on a screen through a graphics user interface (GUI). The ultrasound image generating apparatus 1000 may include two or more the display units 390 depending on an implementation type.

The embodiments of the present invention may be written as computer programs and may be implemented in general-use digital computers that execute the programs using a computer readable recording medium.

Examples of the computer readable recording medium include magnetic storage media (e.g., ROM, floppy disks, hard disks, etc.) and optical recording media (e.g., CD-ROMs, or DVDs).

It should be understood that the exemplary embodiments described herein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. A method of generating an ultrasound image in an ultrasound image generating apparatus having an ultrasound probe, a hardware processor, and a display, by changing a level of a signal on a scan line depending on an acquired position and amplitude of an ultrasound response signal, the method comprising:
 acquiring, through the ultrasound probe connected to the ultrasound image generating apparatus, a response signal to an ultrasound wave transmitted to an object;
 changing, using the hardware processor of the ultrasound image generating apparatus, a level of the acquired response signal depending on a position and an amplitude of the acquired response signal on a scan line, using a decompression gain that changes based on depth, measured from the ultrasound probe, to enhance a distinction between the response signal and noise generated in the ultrasound image generating apparatus;
 performing, using the hardware processor of the ultrasound image generating apparatus, logarithmic compression on the level-changed response signal;
 generating, using the hardware processor of the ultrasound image generating apparatus, an ultrasound image based on the compressed signal; and
 displaying, on the display of the ultrasound image generating apparatus, the ultrasound image.

2. The method of claim 1, wherein the changing of the level is performed by multiplying an amplitude of envelop data included in the response signal by a decompression coefficient.

3. The method of claim 2, wherein the decompression coefficient is determined based on at least one of a decompression value, a dynamic range, a minimum detection level of ultrasound signal amplitude, and an amplitude of envelop data.

4. The method of claim 3, wherein the decompression value is determined depending on a position of each pixel indicating the ultrasound image.

5. The method of claim 3, wherein the decompression value is preset according to a predetermined reference or is set in real time according to a user input.

6. The method of claim 2, wherein the decompression coefficient is determined via the equation below:

$$\alpha(s, z) = 10^{\{(\frac{DR}{DR-DV(s,z)}-1)\cdot(20\cdot\log_{10}(x(s,z)))+(1-\frac{DR}{DR-DV(s,z)})\cdot Min(s,z)\}/20}$$

where S denotes a scan line position value, z denotes a depth position value, a(s, z) is a decompression coefficient at coordinates (s, z), DR denotes a dynamic range, DV(s, z) denotes a decompression value at coordinates (s, z), MIN(s, z) denotes a minimum detection level of ultrasound signal amplitude at coordinates (s, z), and x(s, z) denotes an amplitude of envelop data at coordinates (s, z).

7. An apparatus for generating an ultrasound image by changing a level of a signal on a scan line depending on an acquired position and amplitude of an ultrasound response signal, the apparatus comprising:
an ultrasound probe;
a display;
a hardware processor; and
a memory storing instructions that, when executed by the hardware processor perform operations comprising:
acquiring, through the ultrasound probe, a response signal to an ultrasound wave transmitted to an object;
changing a level of the acquired response signal depending on a position and amplitude of the acquired response signal on a scan line, using a decompression gain that changes based on depth, measured from the ultrasound probe, to enhance a distinction between the response signal and noise generated in the ultrasound image generating apparatus;
logarithmically compressing the level-changed response signal; and
generating an ultrasound image based on the compressed signal for display on the display.

8. The apparatus of claim 7, wherein the hardware processor changes the level of the response signal by multiplying an amplitude of envelop data included in the response signal by a decompression coefficient.

9. The apparatus of claim 8, wherein the decompression coefficient is determined based on at least one of a decompression value, a dynamic range, a minimum detection level of ultrasound signal amplitude, and an amplitude of envelop data.

10. The apparatus of claim 9, wherein the decompression value is determined depending on a position of each pixel indicating the ultrasound image.

11. The apparatus of claim 9, wherein the decompression value is preset according to a predetermined reference or is set in real time according to a user input.

12. The apparatus of claim 8, wherein the decompression coefficient is determined via the equation below:

$$\alpha(s, z) = 10^{\{(\frac{DR}{DR-DV(s,z)}-1)\cdot(20\cdot\log_{10}(x(s,z)))+(1-\frac{DR}{DR-DV(s,z)})\cdot Min(s,z)\}/20}$$

where S denotes a scan line position value, z denotes a depth position value, a(s, z) is a decompression coefficient at coordinates (s, z), DR denotes a dynamic range, DV(s, z) denotes a decompression value at coordinates (s, z), MIN(s, z) denotes a minimum detection level of ultrasound signal intensity at coordinates (s, z), and x(s, z) denotes an amplitude of envelop data at coordinates (s, z).

* * * * *